(12) United States Patent
Gerstmar

(10) Patent No.: US 6,595,935 B2
(45) Date of Patent: Jul. 22, 2003

(54) CERVICAL SUPPORT STRUCTURE

(75) Inventor: Gail L. Gerstmar, Tigard, OR (US)

(73) Assignee: Caddy Company, LLC, Tigard, OR (US)

( * ) Notice: Subject to any disclaimer, the term of this patent is extended or adjusted under 35 U.S.C. 154(b) by 0 days.

(21) Appl. No.: 09/952,359

(22) Filed: Sep. 12, 2001

(65) Prior Publication Data

US 2003/0050580 A1 Mar. 13, 2003

(51) Int. Cl.[7] .................................................. A61F 5/00
(52) U.S. Cl. ............................................................ 602/1
(58) Field of Search .............................. 602/1, 17–19; 128/97.1, 61–63

(56) References Cited

U.S. PATENT DOCUMENTS

| | | | | |
|---|---|---|---|---|
| 4,576,150 A | * | 3/1986 | Auracher | 602/18 |
| 4,934,357 A | * | 6/1990 | Frantzich et al. | |
| 5,271,114 A | * | 12/1993 | Kjersem | 5/640 |
| 5,275,581 A | * | 1/1994 | Bender | 602/18 |
| 5,685,613 A | * | 11/1997 | Franzen, Jr. | 297/397 |
| 5,722,939 A | * | 3/1998 | Hohlen | 602/18 |
| 5,904,662 A | * | 5/1999 | Myoga | 602/18 |
| 5,979,456 A | * | 11/1999 | Magovern | 128/899 |
| 6,009,577 A | * | 1/2000 | Day | |
| 6,056,711 A | * | 5/2000 | Domanski et al. | 602/18 |
| 6,071,255 A | * | 6/2000 | Calabrese | 602/18 |

* cited by examiner

Primary Examiner—Nicholas D. Lucchesi
Assistant Examiner—Lalita M Hamilton
(74) Attorney, Agent, or Firm—Jon M. Dickinson, PC; Robert D. Varitz, PC

(57) ABSTRACT

A cervical support structure which includes an elongate collar that is removably wrappable about a user's neck, a size-adjustable, pillow-receiving sling structure effectively joined to the outside surface of the collar, and pillow structure which can be removably received by the sling structure to function as a pillow support element cooperating with the collar in the providing of cervical support.

3 Claims, 3 Drawing Sheets

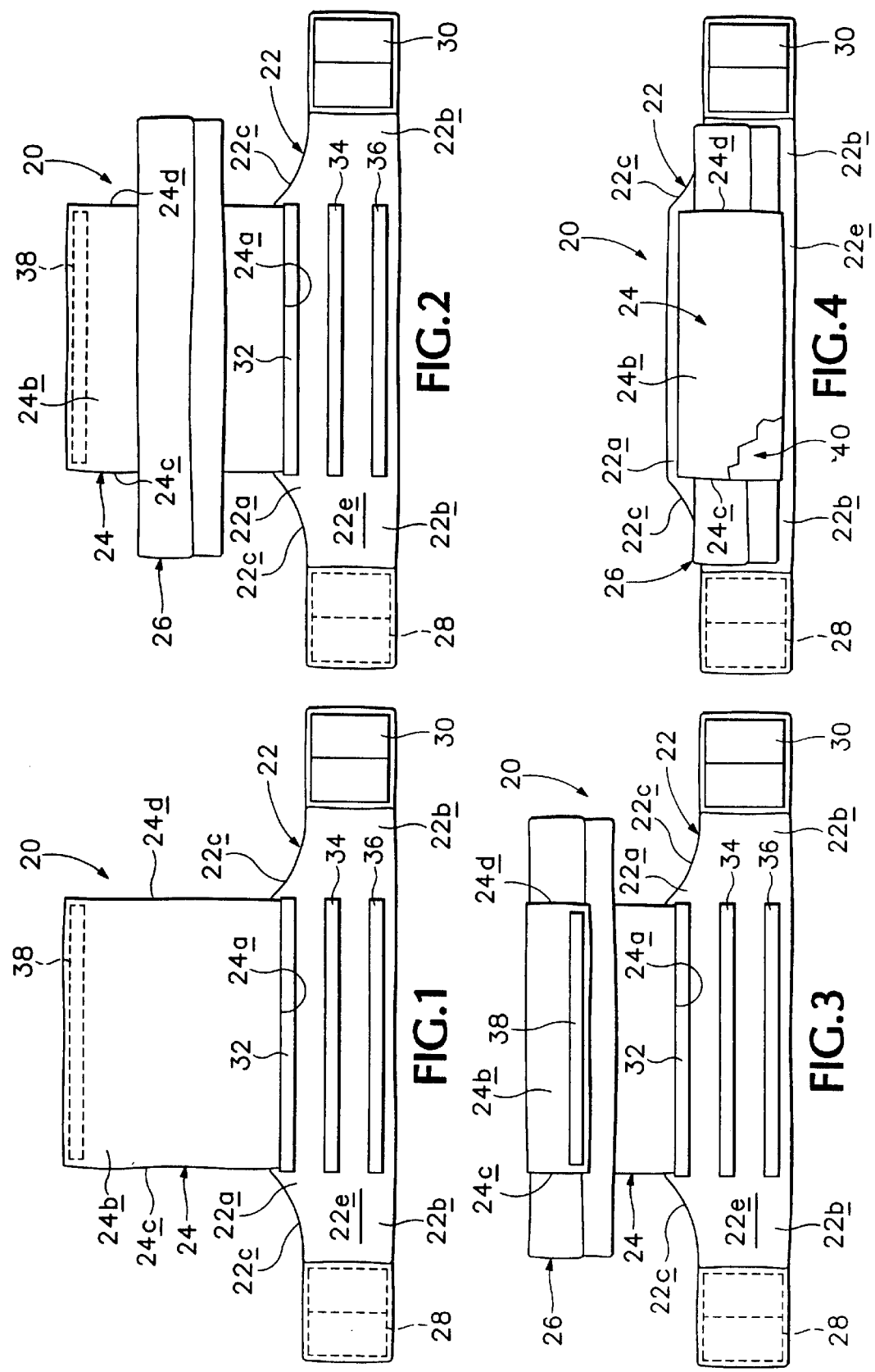

CERVICAL SUPPORT STRUCTURE

BACKGROUND AND SUMMARY OF THE INVENTION

The present invention relates to cervical support structure, and in particular, to such structure which includes an elongate cervical collar element to which, on the outside, there, is attached a pillow sling structure that is adapted to receive removably a pillow structure, such as a rolled up towel.

There are many applications for cervical support structures. These typically take the form of an elongate cushioning collar that can be wrapped around a wearer's neck, or of a specially configured pillow which is generally free from a user, and used with the user lying down and the back of the neck supported on the pillow. While both of these prior art cervical support devices have utility, the present invention recognizes a unique way, and furnishes a unique structure, for combining these dual utilities.

In its fully operative condition with respect to a user, the collar element of this invention is wrapped circumferentially, removably about the user's neck, and an elongate, preferably cylindrical pillow is attached removably to the back of the collar element through the mentioned sling structure. The sling structure forms an elongate, selectively sizeable, double-open-ended tube that receives and holds the pillow. According to one preferred form of the invention, all of the elements of the invention are sized in such a manner that the opposite ends of the pillow jut outwardly beyond the opposite ends of the receiving tube formed by the sling structure. These ends extend somewhat as wings toward laterally opposite sides of the user's neck and head, and among other things, allow the user to roll the head, or the whole body, to the side without losing pillow support.

This combinational structure offers a user substantially all of the advantages of the mentioned, individual prior art cervical devices.

These and other features and advantages which are offered and attained by the present invention will become more fully apparent as the description which now follows is read in conjunction with the accompanying drawings.

DESCRIPTION OF THE DRAWINGS

FIGS. 1–4, inclusive, show different plan views of one preferred form of the cervical support structure of the present invention, illustrated in different stages of preparation for wearing and use by a user.

DETAILED DESCRIPTION OF THE INVENTION

Figure 5:
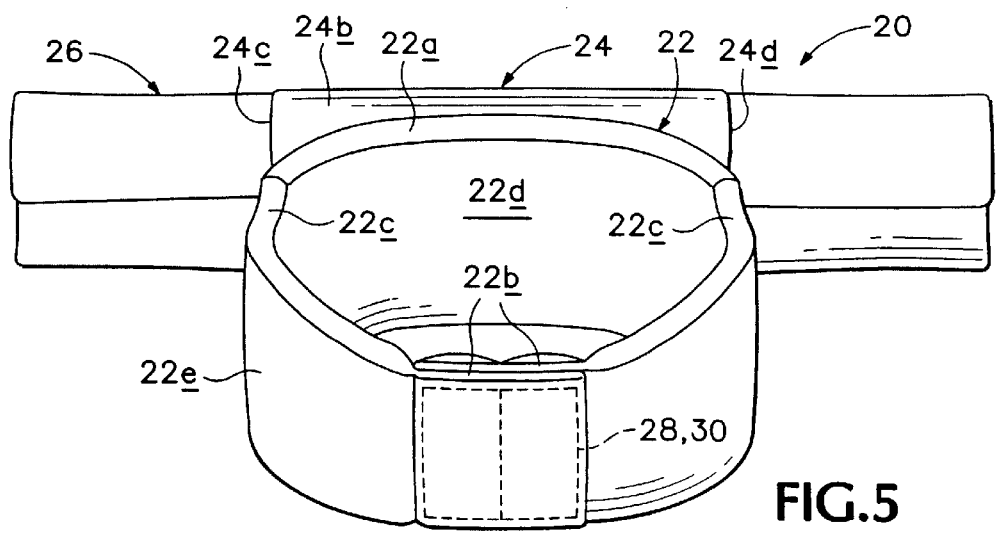
FIGS. 5 and 6 picture several different use conditions for the invention of FIGS. 1–4, inclusive.

Turning now to the drawings, and referring first of all to FIGS. 1–4, inclusive, indicated generally at 20 is a preferred embodiment of a cervical support structure which is constructed in accordance with the present invention. Support structure 20 includes an elongate collar 22, a pillow sling structure 24, and one form of pillow, shown at 26 in FIGS. 2, 3 and 4.

Collar 22 generally has the contoured configuration shown with a high-contour or wider central region 22a and a low contour narrower pair of end regions 22b. Region 22a joins with regions 22b through concavely-curved regions 22c.

Collar 22 is preferably formed of conventional materials including a cushioning foam core of any appropriate softness and/or firmness, with this core being covered by medical-grade stockinet material, such as seamless, cotton-knit tubing. The specific materials employed to make up collar 22 are not elements of the present invention, and thus are described herein in no further detail.

Suitably attached adjacent the outer ends of collar regions 22b are conventional hook-and-loop fasteners, such as Velcro®, 28, 30, which accommodate removable securing of the collar to form an appropriate supportive circumferential structure about a user's neck. FIG. 5 illustrates (isolated from any user) such a configuration for collar 22.

Continuing now with reference to FIG. 5 along with FIGS. 1–4, inclusive, collar 22 is seen to include an inside surface 22d and an outside surface 22e. Suitably attached centrally to outside surface 22e, within the lateral extent of central region 22a, are elongate strips 32, 34, 36 which are alike in construction, and each of which takes the form of what can be thought of as one-half of a hook-and-loop, releasable attaching structure, such as that previously mentioned. While three of these strips only are illustrated herein, it should be understood that a greater or lesser number could be employed. Also, the relative size proportions of these strips can differ according to the selected application for use of the structure of this invention.

Attached (in the embodiment now being described herein) along one side of strip 32 is an edge 24a in a fabric-like flap 24b which makes up pillow sling structure 24. Attached to the upper free edge of flap 24b in FIGS. 1 and 2, and on the far side of the flap in these two figures, is another elongate fastener strip 38 which is designed to coact with any one of strips 32, 34, 36 in a hook-and-loop manner, effectively to close the sling flap upon itself, and to form an elongate, hollow receiving tube extending along the central outside region of collar 22. Lateral edges 24c, 24d, the spaced side edges in flap 24b, form the edges of such a tube which is shown generally near a jagged breakaway in FIG. 4 at 40. Such rolling of flap 24b to form a tube can be done in such a fashion as to form many different tubes with differing cross-sectional areas, depending upon to which one of strips 32, 34, 36, 38 becomes attached.

Pillow structure 26 herein takes the form of a rolled towel which, when rolled as generally shown in FIGS. 2–5, inclusive, forms an elongate cylindrical structure designed to be removably received in a formed receiving tube of the type just previously discussed with respect to operation of pillow sling structure 24. In FIG. 1, the pillow structure is absent. In FIG. 2, the pillow structure has been placed on the fully developed form of flap 24b, and in FIG. 3, curling or rolling of flap 24b is partially underway to create a receiving tube for the pillow structure. In FIG. 4, tube 40 is completely formed, and pillow structure 26 is seen to be confined within this tube, with the opposite ends of the cylindrical form of the pillow structure extending laterally outwardly as wings beyond the opposite ends of tube 40. Preferably, and as can be seen quite easily in FIGS. 4 and 5, with the pillow structure effectively joined to the collar and disposed within tube 40, the pillow structure is essentially supported along much of its length within tube 40, whose supporting length generally matches the long dimension of the central region in collar 22.

It should be evident that while a particular rolled, towel-like pillow structure is disclosed herein, such a pillow structure, which preferably has a cylindrical form, can be prepared in a number of different ways, and specifically can have different selected final rolled or cylindrical diameters, depending upon the application and the user's wishes. Thus, the structure of the invention contemplates allowing for significant size adaptability in this region, such adaptability being accommodated especially by the structure proposed for the pillow sling structure and for the attaching and closure devices, such as strips 32, 34, 36, that are provided for forming pillow-structure receiving tubes.

In use, a user prepares the structure of the invention to have generally the form pictured in FIG. 4. The user then wraps the collar circumferentially about his or her neck, and appropriately closes the opposite collar ends upon themselves to form a comfortable fit around the neck, such as is pictured in FIG. 8. In this condition, one will see that the configuration preferred for the perimetral outline in collar 22 results in curved regions 22c lying generally along the jaw ridge line area extending from slightly underneath the ears, downwardly along and under the jaw toward the space underneath the chin. The opposite ends of pillow structure 26 extend laterally beyond the closed collar as laterally extending wings, such as those that are clearly seen in FIG. 8.

Figure 8:
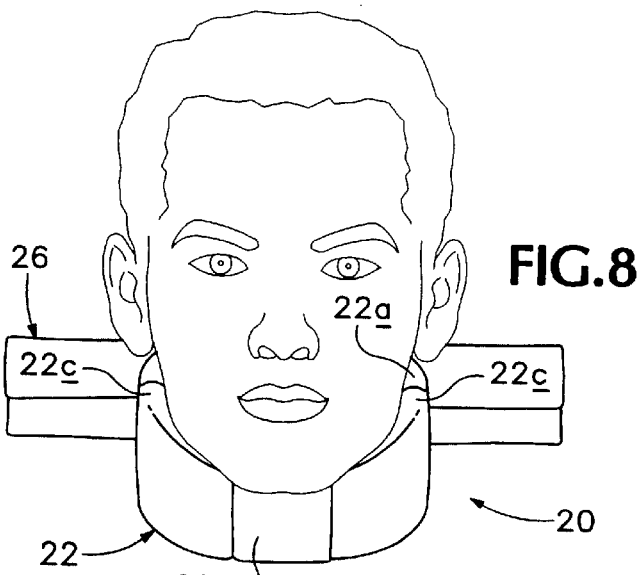
FIGS. 8–10, inclusive, picture the embodiment of the invention of FIGS. 1–4, inclusive, being worn by a user.
Figure 10:
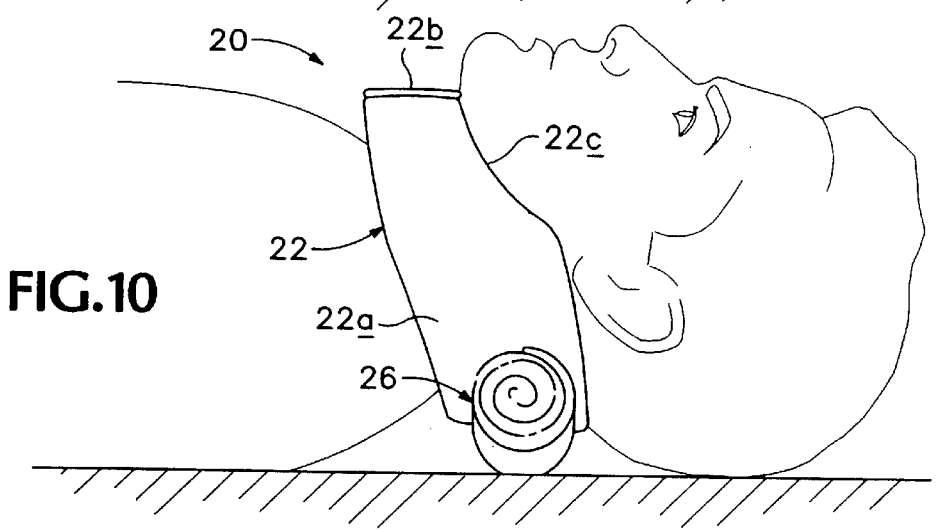

With the structure of this invention installed for use as pictured in FIG. 8, then, with the user simply lying on his or her back, with the face looking straight up, the central, rear region of the neck is given substantial support both by the collar structure, and by the pillow structure which works as a unit with the collar structure according to the invention. The portions of the collar structure which extend forwardly and beneath the chin stabilize the head. FIG. 10 illustrates a side view which is rotated clockwise relative to a view taken along the right side of FIG. 8, and shows this important support condition.

Figure 6:
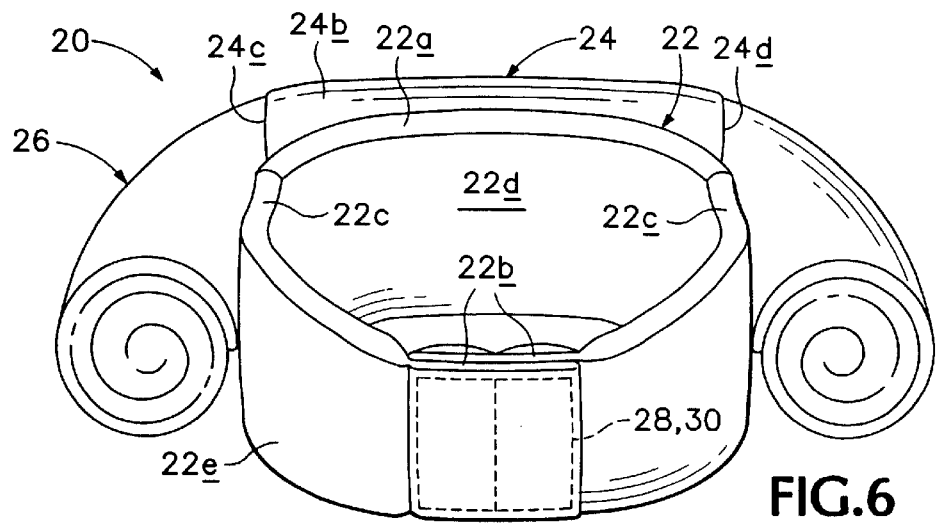
Figure 9:
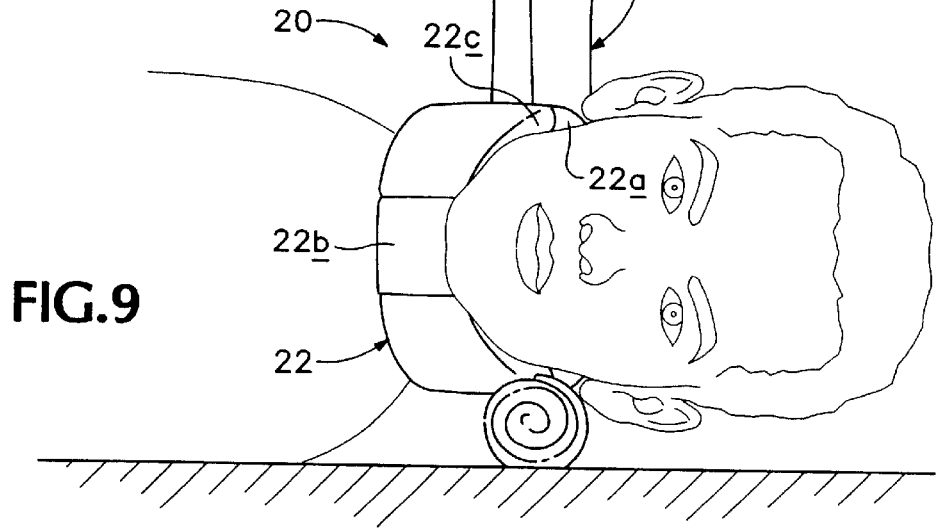

With the device installed as shown and described, if the user rolls the head and neck, or the whole body, toward one side, such as toward the viewer as shown in FIG. 9, the appropriate extending wing end of the pillow structure bends and curves to accommodate this positional adjustment, and does so specifically in a manner which continues to provide combined collar and pillow support for what is now the side region of the wearer's neck. FIG. 6 in the drawings illustrates such a condition with the extending ends of the pillow structure in this figure each being shown so bent and curved to indicate the bilateral accommodation capability of the structure of this invention.

Preferably, all components of the invention are made of materials which permit cleaning and repetitive multiple uses. Over time, a user can vary the support characteristics of the device of this invention simply by varying the shapes and sizes of the pillow structure.

Figure 7:
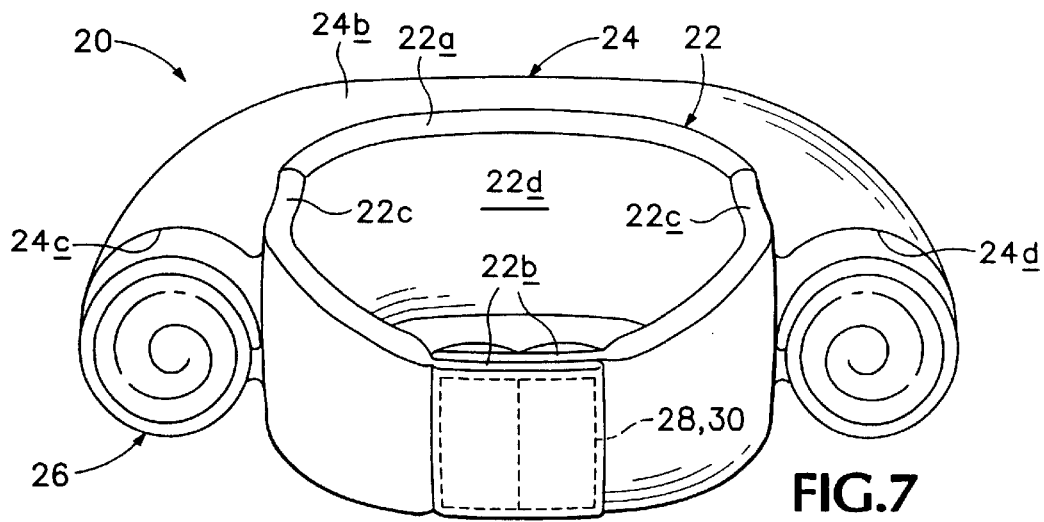
FIG. 7 shows a modified form of the invention.

FIG. 7 in the drawings illustrates one useful modification wherein sling structure 24 has been constructed with significantly greater overall lateral dimensions so as to form, with the collar curved around a user's neck, an elongate curved tube adapted to receive an installed pillow structure. In this embodiment, a pillow structure is supported along a significantly greater length than that length of the support provided by the pillow sling structure of the other drawing figures herein.

It should be clear, from the description that has been given herein of the present invention, that various dimensions can easily be changed and employed to suit a wide range of different applications (i.e., head sizes, neck sizes, etc.).

Accordingly, while a preferred embodiment of the invention, and a manner of practicing it, have been illustrated and described herein, it is understood that variations and modifications may be made without departing from the spirit of the invention.

I claim:

1. Cervical support structure comprising
    an elongate collar having inside and outside surfaces wrappable and adjustably securable to provide circumferential support about a user's neck, and
    pillow-sling structure joined to and operable fully and solely on said collar's outside surface, adapted for the removable receipt of an elongate pillow structure with such disposed adjacent and outwardly of the outside surface of said collar, and toward the rear thereof when the collar is wrapped around a user's neck.

2. The support structure of claim 1, wherein adjustable fastening of said free edge to said collar allows for the formation of different-configuration pillow-receiving tubes having different nominal cross-sectional areas and shapes as such are viewed generally along the long axis of a formed tube.

3. The support structure of claim 1, wherein the spacing between said lateral edges is roughly the same as the nominal outside diameter of the mentioned circumferential support which exists about a user's neck with the collar wrapped around the neck.

\* \* \* \* \*

UNITED STATES PATENT AND TRADEMARK OFFICE
CERTIFICATE OF CORRECTION

PATENT NO.    : 6,595,935 B2
DATED         : July 22, 2003
INVENTOR(S)   : Gail L. Gerstmar It is certified that error appears in the above-identified patent and that said Letters Patent is hereby corrected as shown below:

<u>Column 4,</u>
Lines 25-35, Claim 1 should read:

1.    Cervical collar support structure comprising:
       an elongate, circumferential neck-wrap, cervical collar having inside and outside surfaces which are defined as such when the collar is wrapped circumferentially about a user's neck, said cervical collar including a central region which, with the collar so wrapped around the neck, resides adjacent the central, rear, cervical region of the neck,
       pillow-sling structure joined to and operable fully and solely on said cervical collar's outside surface at the location of the collar's said central region, adapted for the removable receipt of an elongate pillow structure with such disposed adjacent, outwardly and rearwardly of the outside surface of said collar's said central region, and
       first and second attaching structures joined to a rear outside surface of said collar,
       said pillow-sling structure including a flap of flexible material with a span having one perimetral edge secured to said collar by way of said first attaching structure, and an opposite, free perimetral edge which is releasably and adjustably fastenable to said collar by way of said second attaching structure, and further including a pair of spaced, lateral, perimetral edges which, together with the span of said flap, cooperate to form on the outside only of said collar an elongate, hollow, pillow-receiving, double-open-ended, freely configurable tube under circumstances with said free edge fastened to the collar, the length of said tube being generally defined by the spacing between said lateral edges.

Signed and Sealed this

Ninth Day of December, 2003

JAMES E. ROGAN
*Director of the United States Patent and Trademark Office*